United States Patent [19]

Hungerbühler et al.

[11] Patent Number: 4,962,196

[45] Date of Patent: Oct. 9, 1990

[54] (3S, 4R)-3,4-TRANS-DISUBSTITUTED AZETIDIN-2-ONE INTERMEDIATES

[75] Inventors: Ernst Hungerbühler, Rheinfelden; Jaroslav Kalvoda, Binningen, both of Switzerland

[73] Assignee: Ciba-Geigy Corporation, Ardsley, N.Y.

[21] Appl. No.: 331,072

[22] Filed: Mar. 24, 1989

Related U.S. Application Data

[63] Continuation of Ser. No. 203,534, May 24, 1988, which is a continuation of Ser. No. 902,804, Sep. 2, 1986, abandoned.

[30] Foreign Application Priority Data

Sep. 11, 1985 [CH] Switzerland ............ 3928/85-3
Mar. 6, 1986 [CH] Switzerland ............ 919/86-5

[51] Int. Cl.⁵ .............. C07D 205/09; C07D 403/12; C07D 417/12; C07B 51/00
[52] U.S. Cl. ............................ 540/357; 540/310
[58] Field of Search ............................ 540/357

[56] References Cited

U.S. PATENT DOCUMENTS

| | | | |
|---|---|---|---|
| 4,347,183 | 8/1982 | Afonso et al. | 260/245.2 |
| 4,540,579 | 9/1985 | Afonso | 540/310 |
| 4,656,165 | 4/1987 | Lang | 540/310 |
| 4,826,832 | 5/1989 | Lang | 514/192 |

FOREIGN PATENT DOCUMENTS

| | | | |
|---|---|---|---|
| 900477 | 8/1984 | Belgium | 540/357 |
| 125208 | 11/1984 | European Pat. Off. | |
| 2144743 | 3/1985 | United Kingdom | |

OTHER PUBLICATIONS

J. Rigaudy et al., Nomenclature of Organic Chemistry (1979 Edition), p. 66.
Paterson, Austin M. American Chemical Society.
J. Am. Chem. Soc. vol. 104, No. 22 pp. 6138 (1982).

Primary Examiner—Mark L. Berch
Attorney, Agent, or Firm—JoAnn Villamizan

[57] ABSTRACT

The invention relates to an improved process for the preparation of compounds of formula

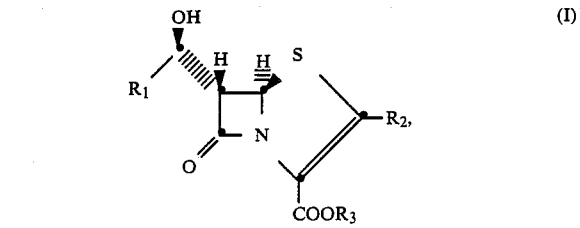

or salts thereof, starting from compounds of formulae

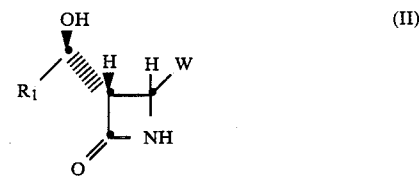

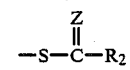

via compounds of formulae

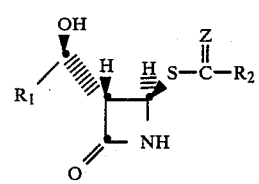

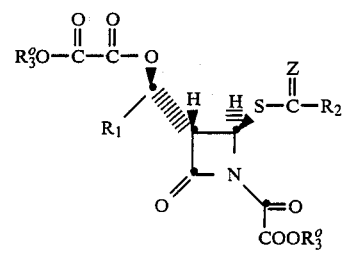

and

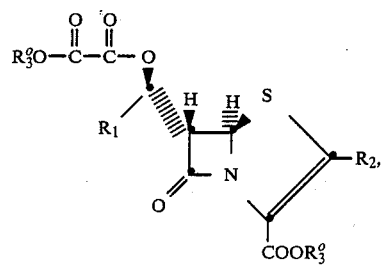

in which compounds $R_1$ is hydrogen or lower alkyl, $R_2$ is an organic radical which may carry a functional group which may be protected by a customary protective group $R_2^0$, $R_3$ is hydrogen or a customary carboxyl protective group $R_3^0$, W is a group which can be replaced by a thiocarboxylic acid radical of formula III, and Z is oxygen or sulfur.

6 Claims, No Drawings

(3S, 4R)-3,4-TRANS-DISUBSTITUTED AZETIDIN-2-ONE INTERMEDIATES

This application is a continuation, of application Ser. No. 203,534, filed 5/24/88 which is a continuation of Ser. No. 902,804 filed 9/2/86 both now abandoned.

The present invention relates to an improved process for the preparation of compounds of formula

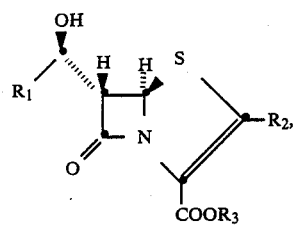  (I)

or salts thereof, which comprises
(a) treating a compound of formula

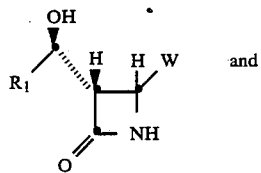  (II)

and with a compound that introduces a thiocarboxylic acid radical of formula

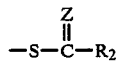  (III)

(b) treating a resultant compound of formula

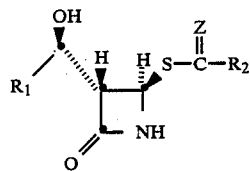  (IV)

with an acylating agent that introduces the acyl radical of an oxalic acid hemiester of formula

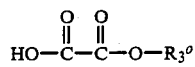  (V)

(c) treating a resultant compound of formula

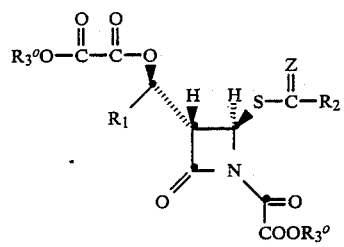  (VII)

with an organic compound of trivalent phosphorus, and
(d) removing the oxalyl ester group —CO—COO—$R_3^o$ and, if desired, the protective group $R_3^o$ and/or a protective group $R_2^o$ which may be present in the radical $R_2$, in any order, from a resultant compound of formula

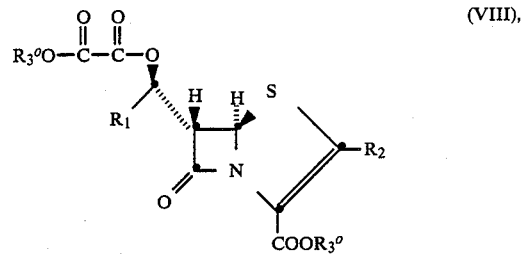  (VIII), and replacing said group or groups with hydrogen and, if desired, converting a resultant compound of formula I containing a salt-forming group into a salt or converting a resultant salt into the free compound, in which compounds $R_1$ is hydrogen or lower alkyl, $R_2$ is an organic radical which may carry a functional group which may be protected by a customary protective group $R_2^o$, $R_3$ is hydrogen or a customary carboxyl protective group $R_3^o$, W is a group which can be replaced by a thiocarboxylic acid radical of formula III, and Z is oxygen or sulfur.

The improvement of the process of this invention resides in a number of surprising features. Thus it is especially surprising that the use of the compound of formula II, wherein the hydroxyl group is unprotected, in the thiolisation reaction (step a) affords almost exclusively the 3,4-trans-compound of formula IV. Up to now it has always been customary to provide this hydroxyl group with a protective group, but with the result that the 3,4-cis-compound has always been formed as by-product in the subsequent thiolisation step. It is therefore a considerable advantage that the 1'-hydroxy groups in the intermediates of formulae II and IV do not need to be protected selectively, as has been usual up to now, by other acyl groups or by silyl groups, and that, in a single step, the compound of formula IV is substituted at the azetidinone nitrogen with the acyl radical of the oxalic acid hemiester required for the cyclisation, as well as protectively at the hydroxy group in 1'-position with the same acyl radical.

It is also surprising that the phosphorane obtained perforce as intermediate is formed only at the β-lactam-N-adjacent carbonyl (step c), and that the theoretically possible reaction with the carbonyl group of the 1'-oxalyl ester group does not take place.

Finally, the improvement of the process of this invention resides in the surprising feature that the acyl radical of the oxalic acid hemiester of formula (V) can be removed extremely easily from the intermediate of formula VIII, i.e. without isomerisation or other damage to the penem ring structure and, as desired and depending on the reaction conditions, replaced either selectively or simultaneously by the other protective groups $R_2^o$ or $R_3^o$ or by hydrogen.

A host of penem compounds of formula I are known and the substituents $R_1$, $R_2$ and $R_3$ have in particular the known meanings.

Compounds of formula I which can be prepared by the process of this invention are disclosed e.g. in the following patent specifications:

Ciba-Geigy GB No. 2.013.676, EP Nos. 109 362, 110 826, 112 283, 125 208, 125 207, BE No. 9 00 477, EP No. 148 128; Beecham EP No. 46 363; Bristol Myers NL Nos. 7909 055, 7 909 056; U.S. Pat. No. 4,282,150; Farmitalia BE No. 881 862, GB No. 2 097 786, DE No. 3 312 393, BE No. 900 316; Hoechst EP No. 69 377, GB No. 2 122 619, GB No. 2 140 807; Merck EP Nos. 2 210, 72 014, 87 792, 115 308; Pfizer EP No. 130 025, 132 101; Sankyo BE No. 889 151, DE No. 3 231 596; Schering Corp. U.S. Pat. No. 4,443,463, BE No. 881 012, U.S. Pat. No. 4,423,055, EP Nos. 35 188, 58 317, U.S. Pat. Nos. 4,431,654, 4,435,412, 4,435,413, 4 503 064, EP Nos. 109 044, 118 875, 123 650, 121 502; Shionogi EP No. 115 969; Sumitomo EP No. 70 204, 126 587; Takeda EP No. 69 373.

The definitions of the substituents $R_1$, $R_2$ and $R_3$ cited in these publications are incorporated herein by reference.

The substituents $R_1$, $R_2$, $R_2^o$, $R_3$, $R_3^o$, W and Z in formulae I to VIII have in particular the following meanings, in which connection the term "lower" qualifying groups and compounds denotes that said groups and compounds, unless otherwise expressly stated, contain 1 to 7, preferably 1 to 4, carbon atoms.

$R_1$ as lower alkyl is preferably methyl or also ethyl, propyl, isopropyl or butyl. Those compounds are preferred in which $R_1$ is hydrogen or, preferably, methyl.

$R_2$ is preferably e.g. an organic radical, known in penem chemistry, containing up to 18, preferably up to 10 and, most preferably, up to 5 carbon atoms, and which may contain up to 5, preferably up to 4, nitrogen atoms, and/or up to 5, preferably up to 2, oxygen atoms, and/or up to 3, preferably 2, sulfur atoms or, most preferably, 1 sulfur atom, and which may be attached to the penem ring through one of its carbon atoms as well as through a nitrogen, oxygen or sulfur atom, and is e.g. unsubstituted or substituted lower aliphatyl, lower aliphatyloxy, lower aliphatylthio, cycloaliphatyl, cycloaliphatyloxy, cycloaliphatylthio, aryl, aryloxy, arylthio, aryl-lower aliphatyl, aryl-lower aliphatyloxy, aryl-lower aliphatylthio, heterocyclyl, heterocyclyloxy, heterocyclylthio, heterocyclyl-lower aliphatyl, heterocyclyl-lower aliphatyloxy, heterocyclyl-lower aliphatylthio, heterocyclyloxy-lower aliphatyl or heterocyclylthiolower aliphatyl, with lower aliphatyl, cycloaliphatyl and heterocyclyl being saturated or unsaturated.

Lower aliphatyl is e.g. lower alkyl, also lower alkenyl, and lower aliphatyloxy or lower aliphatylthio is a suitable lower aliphatyl radical which is bound through an oxygen or sulfur atom.

Cycloaliphatyl is for example cycloalkyl or unsaturated cycloalkyl such as cycloalkenyl or cycloalkadienyl. Cycloaliphatyloxy or cycloaliphatylthio is a corresponding cycloaliphatyl radical which is bound through an oxygen or sulfur atom.

Aryl is for example a suitable monocyclic or also polycylic radical, e.g. a bicyclic radical, preferably phenyl or naphthyl.

Aryloxy or arylthio is an appropriate aryl radical which is bound through an oxygen or sulfur atom. Aryl-lower aliphatyl, aryl-lower aliphatyloxy or aryl-lower aliphatylthio is for example phenyl-lower alkyl, phenyl-lower alkoxy or phenyl-lower alkylthio.

Heterocyclyl, heterocyclyloxy or heterocyclylthio is preferably a suitable monocyclic or polycyclic, preferably monocyclic or bicyclic, radical or also a tricyclic radical, for example an unsaturated or partially saturated monocyclic 5- to 6-membered heteroaryl radical containing at least one hetero atom selected from the group consisting of nitrogen, oxygen and sulfur, in particular a radical of this type containing ring nitrogen atoms and which may contain an additional ring hetero atom selected from oxygen and sulfur, for example a suitable aza-, diaza-, triaza-, tetraza-, oxa-, oxaza-, oxadiaza-, oxatriaza-, thia-, thiaza-, thiadiaza- or thiatriaza-cyclic radical of aromatic character or a suitable dihydro or tetrahydro radical, and also an unsaturated or partially saturated benzo, dibenzo, pyrido or pyrimido derivative of such a 5- or 6-membered radical. Suitable heteroaryl radicals are e.g. pyrrolyl such as 2- or 3-pyrrolyl, 2- or 3-pyrrolidinyl, diazolyl such as imidazolyl, e.g. 1-, 2-, 4- or 5-imidazolyl, or pyrazolyl, e.g. 3- or 4-pyrazolyl, triazolyl, e.g. 1,2,3-triazol-4-yl, 1,2,4-triazol-5-yl or 1,2,4-triazol-3-yl tetrazolyl, e.g. 1H- or 2H-tetrazol-5- or -1-yl, pyridyl, e.g. 2-, 3- or 4-pyridyl, diazinyl such as pyrimidyl, e.g. 2-, 4- or 5-pyrimidyl, or pyrazinyl, e.g. 2-pyrazinyl, triazinyl, e.g. 1,2,4-triazin-6-yl or 1,3,5-triazin-2-yl, furyl, e.g. 2- or 3-furyl, 2- or 3-tetrahydrofuryl, thienyl, e.g. 2-or 3-thienyl, oxazolyl, e.g. 2- or 4-oxazolyl, oxadiazolyl, e.g. 1,2,4-oxadiazol-3-yl, 1,2,5-oxadiazol-3-yl, 1,2,4-oxadiazol-5-yl or 1,3,4-oxadiazol-2-yl, isoxazolyl, e.g. 3-isoxazolyl, thiazolyl, e.g. 2- or 4-thiazolyl, thiadiazolyl, e.g. 1,2,4-thiadiazol-3-yl, 1,2,5-thiadiazol-3-yl, 1,2,4-thiadiazol-5-yl or 1,3,4-thiadiazol-2-yl, or isothiazolyl, e.g. 3- or 4-isothiazolyl. The cited 5- and 6-membered heteroaryl radicals may also be in partially saturated form. Examples of such radicals are dihydroimidazolyl, e.g. 2,3-dihydroimidazol-4-yl, dihydropyridyl, e.g. 1,2-dihydropyrid-3-yl, dihydropyrimidyl, e.g. 1,2-dihydropyrimid-4-yl, dihydro- and tetrahydropyrazinyl, e.g. 2,3-dihydropyrazin-5-yl or 3,4,5,6-tetrahydropyrazin-2-yl, or dihydro- or tetrahydrotriazinyl, e.g. 2,3,4,5-tetrahydro-1,2,4-triazin-6-yl. Polycyclic derivatives of the cited heteroaryl radicals are e.g. indol-2-yl, indol-3-yl, benzimidazol-2-yl, benzopyrazol-3-yl, quinolin-2-yl or quinolin-4-yl, benzothiazol-2-, benzoxazol-2-yl, pyrido[2,3-b]pyrid-3-yl or pyrido[2,3-b]pyrid-4-yl.

Heterocyclyl-lower aliphatyl, heterocyclyl-lower aliphatyloxy or heterocyclyl-lower aliphatylthio, heterocyclyloxy-lower aliphatyl or heterocyclylthio-lower aliphatyl are e.g. lower alkyl, lower alkoxy or lower alkylthio radicals that are substituted by one or two heterocyclyl radicals, preferably by one of the above-mentioned heterocyclyl radicals which is bound through one of its carbon atoms or through an oxygen or sulfur atom or by an unsaturated or partially saturated monocyclic 5- or 6-membered heteroaryl radical which is bound through one of its ring nitrogen atoms and which contains from 1 to 4 nitrogen atoms as ring hetero atoms. The last-mentioned radicals which are bound through a nitrogen atom are e.g. imidazol-1-yl, tetrahydro- or 4,5-dihydro-imidazol-1-yl, pyrazol-1-yl, 1,2,4-triazol-1-yl, 1,2,3-triazol-1-yl, tetrazol-1-yl, tetrazol-2-yl, 1-pyridinio, 1,2-dihydro-1-pyridyl, 1,4-dihydro-1-pyridyl, 1,2-dihydro-pyrimid-1-yl or 1,4-dihydro-pyrimid-1-yl. The heterocyclyl radicals may also be attached to the lower aliphatic radical through an oxygen or sulfur atom.

The above organic radicals $R_2$ are unsubstituted or they may be substituted by one or more, preferably by one or two or also three, identical or different members selected from the group consisting of free, etherified or esterified, including protected, hydroxy, e.g. hydroxy, lower alkoxy, phenyl-lower alkoxy, lower alkanoyloxy or halogen; free or etherified mercapto, for example mercapto, lower alkylthio or phenylthio; lower alkyl; lower alkyl substituted by hydroxy, lower alkoxy, free, esterified or amidated carboxy such as carboxy, lower alkoxycarbonyl or carbamoyl, unsubstituted or N-lower alkylated amino, for example amino, lower alkylamino or di-lower alkylamino, lower alkyleneamino, lower alkanoylamino, lower alkoxycarbonylamino which is unsubstituted or substituted by amino and/or carboxy, mercapto, lower alkylthio or sulfo; lower alkylene, unsubstituted or lower alkylated aza-lower alkylene, oxa-, dioxa- or thia-lower alkylene, unsubstituted or substituted, including protected, amino, e.g. amino, lower alkylamino, di-lower alkylamino, lower alkyleneamino, guanidino, carbamoylamino, acylamino such as lower alkanoylamino, or lower alkoxycarbonylamino which is unsubstituted or substituted by amino and/or carboxy; free or functionally modified, including protected, carboxy or sulfo, for example carboxy, esterified carboxy such as lower alkoxycarbonyl, amidated carboxy such as carbamoyl or substituted carbamoyl, for example carbamoyl or N-mono- or N,N-di-lower alkylated carbamoyl, cyano, sulfo or sulfamoyl; phenyl or phenyl which is substituted e.g. by lower alkyl, nitro, amino, hydroxy, lower alkoxy, carboxy and/or by halogen; cycloalkyl; nitro, oxo and/or oxido.

The radicals and substituents thereof mentioned in connection with $R_2$ have for example the following meanings:

Lower alkyl is e.g. n-propyl, isopropyl, n-butyl, isobutyl, sec-butyl or tert-butyl, and also n-pentyl, n-hexyl or n-heptyl, but is preferably methyl or ethyl.

Lower alkenyl is e.g. vinyl, allyl, 2-methylallyl, n-propenyl or isopropenyl.

Lower alkoxy is e.g. methoxy, ethoxy, n-propoxy, isopropoxy, n-butoxy, isobutoxy or tert-butoxy, as well as n-pentyloxy, n-hexyloxy or n-heptyloxy.

Lower alkylthio, is e.g. methylthio or ethylthio, and also n-propylthio, isopropylthio or n-butylthio.

Cycloalkyl preferably contains from 3 to 8, most preferably 5 or 6, ring members and is e.g. cyclopentyl or cyclohexyl, also cyclopropyl and cycloheptyl. Cycloalkenyl contains e.g. 5 or 6 ring members and cycloalkadienyl contains e.g. 6 ring members and are e.g. 1-, 2- or 3-cyclohexenyl, 1- or 2-cyclopentenyl or 1,4-cyclohexadienyl.

Phenyl-lower alkyl is e.g. benzyl, 1-phenylethyl or 2-phenylethyl.

Phenyl-lower alkoxy is e.g. benzyloxy or 1-phenylethoxy.

Lower alkanoyloxy is e.g. formyloxy, acetoxy or propionyloxy.

Halogen is e.g. fluorine, chlorine, bromine or iodine.

Lower alkylamino is e.g. methylamino, ethylamino, n-propylamino, isopropylamino or n-butylamino, and di-lower alkylamino is, for example, dimethylamino, diethylamino, di-n-propylamino or diisopropylamino.

Lower alkyleneamino has preferably from 4 to 6 carbon atoms and is e.g. pyrrolidino or piperidino.

Lower alkanoylamino is e.g. formylamino, acetylamino or propionylamino.

Lower alkoxycarbonylamino which is unsubstituted or substituted by amino and/or by carboxy is, for example, methoxycarbonylamino, ethoxycarbonylamino or isopropoxycarbonylamino, and also 2-amino-2-carboxyethoxycarbonylamino.

Lower alkylene as substituent of the radical $R_2$ may be straight-chain or branched and connects, for example, 2 vicinal carbon and/or hetero atoms of an organic radical $R_2$ by 3 to 5 carbon atoms. Such radicals are, for example, 1,3-propylene, 1,4-butylene, 1- or 2-methyl-1,3-propylene or 2,2-dimethyl-1,3-propylene.

Unsubstituted or lower alkylated aza-lower alkylene, oxa-lower alkylene, dioxa-lower alkylene or thia-lower alkylene is preferably straight-chain but may also be branched and connects, for example, vicinal carbon and/or hetero atoms in the organic radical $R_2$ by 3 to 5 carbon atoms. Examples of such radicals are 1- or 2-aza-1,3-propylene, 1-aza-1,4-butylene, 1-methyl-1-aza-, 1-ethyl-1-aza-, 2-methyl-2-aza- or 2-ethyl-2-aza-1,3-propylene or 1-methyl-1-aza- or 2-methyl-2-aza-1,4-butylene, and also 1-oxa-, 1,3-dioxa-, 1-thia- or 1,3-dithia-1,3-propylene, or 1-oxa-, 1,4-dioxa-, 1-thia- or 1,4-dithia-1,4-butylene.

N-mono-lower alkylated carbamoyl is e.g. N-methylcarbamoyl, N-ethylcarbamoyl or N-propylcarbamoyl. N,N-di-lower alkylated carbamoyl is e.g. N,N-dimethylcarbamoyl or N,N-diethylcarbamoyl.

Lower alkanoyl is e.g. formyl, acetyl or propionyl; lower alkenoyl is e.g. acryloyl; cycloalkanoyl contains 5 to 7 carbon atoms and is e.g. cyclohexanoyl; and phenyl-lower alkanoyl is e.g. phenylacetyl.

Lower alkoxysulfonyl is e.g. methoxysulfonyl or ethoxysulfonyl.

Lower alkoxycarbonyl which may be substituted by amino and carboxy is e.g. methoxycarbonyl, ethoxycarbonyl, n-propoxycarbonyl or 2-amino-2-carboxyethoxycarbonyl.

Lower alkylthiocarbamoyl is e.g. methylthiocarbamoyl or ethylthiocarbamoyl.

Lower alkanesulfonyl is e.g. methanesulfonyl, ethanesulfonyl or propanesulfonyl.

Suitable lower aliphatic radicals $R_2$ are e.g. lower alkyl such as methyl, ethyl, isopropyl, isobutyl or sec-butyl, or lower alkyl, preferably methyl, ethyl, n-propyl or n-butyl, which is substituted by hydroxy, lower alkoxy, e.g. methoxy or ethoxy, lower alkanoyloxy, e.g. acetoxy, halogen, e.g. chlorine or bromine, mercapto, lower alkylthio, e.g. methylthio, amino, lower alkylamino, e.g. methyl- or ethylamino, di-lower alkylamino, e.g. dimethylamino, guanidino, formamidino, lower alkanoylamino, e.g. acetylamino, lower alkoxycarbonylamino such as ethoxycarbonylamino which is substituted by amino and carboxy, for example 2-amino-2-carboxyethoxycarbonylamino, carboxy, lower alkoxycarbonyl, for example methoxy- or ethoxycarbonyl, carbamoyl, sulfo, sulfamoyl and/or oxo. Typical representatives of such lower aliphatic radicals $R_2$ are e.g. methyl, isopropyl, isobutyl, sec-butyl, hydroxymethyl, 1- or 2-hydroxyethyl, mercaptomethyl, 2-methylthioethyl, aminomethyl, 1- or 2-aminoethyl, 1-, 2- or 3-aminopropyl, 1, 2- or 3-aminobutyl, guanidylmethyl, 1- or 2-guanidylethyl, 1-, 2- or 3-guanidylpropyl, formamidinomethyl, formamidino-1- or -2-ethyl or formamidino-1-, -2- or -3-propyl, carboxymethyl, carbamoylmethyl, 2-carboxyethyl, 2-carbamoylethyl, carbamoyloxymethyl, 1-, 2- or 3-carbamoyloxypropyl, carboxyl or lower alkoxycarbonyl such as methoxycarbonyl.

Aryl-lower aliphatyl radicals $R_2$ are e.g. unsubstituted or substituted phenyl-lower alkyl, preferably phenylmethyl or phenylethyl, in which the substituents are e.g. lower alkyl such as methyl, nitro, hydroxy, lower alkoxy, e.g. methoxy or ethoxy, carboxy and/or halogen, e.g. chlorine.

Suitable cycloaliphatyl radicals $R_2$ are e.g. cycloalkenyl, for example 1- or 2-cyclohexenyl, or preferably cyclohexadienyl, e.g. 1,4-cyclohexadienyl.

Aryl radicals $R_2$ are e.g. phenyl or phenyl which is preferably substituted by one or also two members selected from the group consisting of amino, lower alkylamino, e.g. methyl- or ethylamino, di-lower alkylamino, dimethylamino, lower alkyl, e.g. methyl, amino-lower alkyl, e.g. 2-aminoethyl, lower alkylamino-lower alkyl, e.g. 2-methylaminoethyl, lower alkoxycarbonylamino-lower alkyl which is substituted by amino and carboxy, for example 2-(amino-2-carboxyethoxycarbonylamino)ethyl, lower alkoxycarbonylamino which is substituted by amino and carboxy, for example 2-amino-2-carboxyethoxycarbonylamino, nitro, hydroxy, lower alkoxy, for example methoxy or ethoxy, halogen, for example chlorine or bromine, and carboxy.

Heterocyclyl radicals $R_2$ are preferably pyrrolyl or dihydropyrrolyl, unsubstituted or substituted e.g. by lower alkyl, for example 1-methyl-2-pyrrolyl or 4,5-dihydro-3-pyrrolyl; pyrrolidyl or oxo-substituted pyrrolidyl, e.g. 2- or 3-pyrrolidyl or 2-oxo-3- or 2-oxo-5-pyrrolidyl, diazolyl such as imidazolyl or pyrazolyl, unsubstituted or substituted e.g. by carboxy, lower alkyl, amino-lower alkyl or amino, for example 1-, 2-, 4- or 5-imidazolyl, 4- or 5-methyl-1-imidazole or 4,5-dimethyl-1-imidazole or 2-amino-4-imidazolyl, or 3-pyrazolyl; triazolyl such as 1H-1,2,3-triazol-4-yl, 1H-1,2,4-triazol-3-yl or 1H-1,2,4-triazol-5-yl, unsubstituted or substituted e.g. by lower alkyl, amino, carboxy-lower alkyl and/or phenyl, for example the corresponding unsubstituted radicals, 1-methyl-1H-1,2,3-triazol-4-yl, 5-methyl- or 5-amino-1H-1,2,4-triazol-3-yl, 3-methyl-1-phenyl-1H-1,2,4-triazol-5-yl, or 5-carboxymethyl- or 5-phenyl-1H-1,2,4-triazol-3-yl; tetrazolyl such as 1H-tetrazol-1-yl, 1H- or 2H-tetrazol-5-yl, unsubstituted or substituted e.g. by lower alkyl, carboxy-lower alkyl, sulfo-lower alkyl, di-lower alkylamino-lower alkyl or by phenyl which may carry substituents such as halogen, for example 1H-tetrazol-1-yl, 1H-tetrazol-5-yl, 1-carboxymethyl-, 1-(2-carboxyethyl)-, 1-(2-sulfoethyl)-, 1-(2-dimethylaminoethyl)- or 1-phenyl-1H-tetrazol-5-yl, thiazolyl such as 2- or 4-thiazolyl, or isothiazolyl such as 3-isothiazolyl, unsubstituted or substituted e.g. by lower alkyl or amino, for example 2-, 4- or 5-thiazolyl, 4-methyl-5- or 5-methyl-4-thiazolyl, 2-amino-4-thiazolyl, 2-amino-4-methyl-5-thiazolyl, 4,5-dimethyl-2-thiazolyl or 3-isothiazolyl; thiadiazolyl such as 1,2,5-thiadiazol-3-yl, 1,3,4-thiadiazol-2-yl, 1,2,4-thiadiazol-3-yl, or 1,2,4-thiadiazol-5-yl, unsubstituted or substituted e.g. by lower alkyl, hydroxy, amino or lower alkylamino, for example the corresponding unsubstituted groups, also 5-methyl- or 5-amino-1,3,4-thiadiazol-2-yl, 3-methyl-1,2,4-thiadiazol-5-yl, 5-amino- or 5-methylamino-1,2,4-thiadiazol-3-yl or 4-hydroxy-1,2,5-thiadiazol-3-yl, oxazolyl or isoxazolyl such as 2- or 4-oxazolyl or 3-isoxazolyl, unsubstituted or substituted e.g. by amino, lower alkyl and/or phenyl, for example the corresponding unsubstituted groups, and also 4-methyl-2-oxazolyl, 4,5-diphenyl-2-oxazolyl, 2-amino-4-oxazolyl or 5-methyl-3-isoxazolyl; oxadiazolyl such as 1,2,4-oxadiazol-5-yl, 1,2,4-oxadiazol-3-yl or 1,3,4-oxadiazol-2-yl, unsubstituted or substituted e.g. by lower alkyl, amino, phenyl or phenyl which is substituted e.g. by nitro, for example the corresponding unsubstituted groups; and also 5-methyl-1,3,4-oxadiazol-2-yl, 5-phenyl-1,3,4-oxadiazol-2-yl or 5-(4-nitrophenyl)-1,3,4-oxadiazol-2-yl, furyl or thienyl such as 2- or 3-furyl or 2- or 3-thienyl, unsubstituted or substituted e.g. by halogen, lower alkyl or by amino-lower alkyl, for example the corresponding unsubstituted groups, 5-methyl- or 5-aminomethyl-2-furyl, or 5-aminomethyl-2-thienyl, tetrahydrofuryl substituted by oxo, e.g. 2-oxotetrahydrofur-5-yl, pyridyl such as 2-, 3- or 4-pyridyl, unsubstituted or substituted e.g. by hydroxy, halogen, lower alkyl, amino and/or by oxido, for example the corresponding unsubstituted groups, 1-oxido-2-pyridyl or 4-chloro-1-oxido-2-pyridyl, or 1,2-dihydropyrimidyl such as 1,2-dihydro-4-pyrimidyl, unsubstituted or substituted e.g. by lower alkyl, amino, di-lower alkylamino, oxo and/or carboxy, for example 2-oxo-1,2-dihydro-4-pyrimidyl or 6-methyl-, 5-methyl-, 6-amino-, 6-dimethylamino-, 5-carboxy- or 6-carboxy-2-oxo-1,2-dihydro-4-pyrimidyl.

Heterocyclyl-lower aliphatic radicals $R_2$ are e.g. unsubstituted or substituted heterocyclylmethyl, heterocyclylethyl or heterocyclylpropyl radicals, for example pyrrol-1-ylmethyl or dihydropyrrol-1-ylmethyl, unsubstituted or substituted e.g. by lower alkyl or halogen, for example pyrrol-1-ylmethyl, 3-methylpyrrol-1-ylmethyl, 3,4-dichloropyrrol-1-methyl, 2,3- or 2,5-dihydropyrrol-1-ylmethyl, unsubstituted or oxo-substituted pyrrolidylmethyl, e.g. 2- or 3-pyrrolidylmethyl or 2-oxo-3-pyrrolidylmethyl or 2-oxo-5-pyrrolidylmethyl, diazolylmethyl such as imidazol-1-ylmethyl, imidazol-4-ylmethyl or pyrazol-1-ylmethyl, unsubstituted or substituted e.g. by lower alkyl; triazolylmethyl such as 1H-1,2,3-triazol-1-ylmethyl, 1H-1,2,4-triazol-1-ylmethyl or 1H-1,2,4-triazol-3-ylmethyl, unsubstituted or substituted e.g. by lower alkyl, carboxy-lower alkyl, amino and/or phenyl, for example the corresponding unsubstituted radicals, 4- or 5-methyl-1,2,3-triazol-1-ylmethyl or 5-methyl-, 5-amino- or 5-phenyl-1H-1,2,4-triazol-3-ylmethyl; tetrazolylmethyl such as 1H-tetrazol-1-ylmethyl, 1H-tetrazol-1-eth-1-yl, 1H-tetrazol-1-eth-2-yl, 1H-tetrazol-1-prop-1-yl, 1H-tetrazol-1-prop-2-yl, 1H-tetrazol-1-prop-3-yl, 2H-tetrazol-2-ylmethyl or 1H-tetrazol-5-ylmethyl, unsubstituted or substituted e.g. by lower alkyl, carboxy-lower alkyl, sulfo-lower alkyl, di-lower alkylamino-lower alkyl, amino or phenyl or phenyl which is substituted by halogen, for example the corresponding unsubstituted radicals, 5-amino-, 5-carboxymethyl-, 5-(2-carboxyethyl)-, 5-sulfomethyl-, 5-(2-dimethylaminoethyl)- or 5-phenyl-1H-tetrazol-1-ylmethyl, 5-amino-, 5-carboxymethyl-, 5-sulfomethyl-, 5-(2-dimethylaminoethyl)- or 5-phenyl-2H-tetrazol-2-ylmethyl, or 1-(2-carboxyethyl)- or 1-(2-dimethylaminoethyl))-2H-tetrazol-5-ylmethyl. pyridylmethyl or dihydropyridylmethyl such as pyridiniomethyl, 2-, 3- or 4-pyridylmethyl or 1,2- or 1,4-dihydropyrid-1-ylmethyl, which is unsubstituted or is substituted preferably by oxo and which may be additionally substituted e.g. by halogen, for example 2-oxo-1,2-dihydropyrid-1-ylmethyl or 4-oxo-1,4-dihydropyrid-1-ylmethyl, dihydropyrimid-1-ylmethyl such as 2H-1,2-dihydro- or 4H-1,4-dihydro-pyrimid-1-ylmethyl, unsubstituted or substituted preferably by oxo and which may be additionally substituted e.g. by lower alkyl, amino, di-lower alkylamino or carboxy, for example 2-oxo-1,2-didhydro-pyrimid-1-ylmethyl, 6-methyl-, 5-methyl-, 6-amino-, 6-dimethylamino-, 5-carboxy- or 6-carboxy-2-oxo-1,2-dihydro-pyrimid-1-ylmethyl or 4-oxo-1,4-dihydropyrimid-1-ylmethyl, furylmethyl, e.g. 2-furylmethyl, tetrahydrofurylmethyl, unsubstituted or substituted by oxo, e.g. 2-oxotetrahydrofur-5-ylmethyl, thienylmethyl, e.g. 2-thienylmethyl, oxazolylmethyl, thiazolylmethyl or thiadiazolylmethyl, unsubstituted or substituted by e.g. amino, e.g. 2-amino-oxazol-4-ylmethyl, 2-aminothiazol-4-ylmethyl or 5-amino-1,2,4-thiadiazol-3-ylmethyl, or indolylmethyl, e.g. indol-3-ylmethyl.

Particularly preferred radicals $R_2$ are those which occur in compounds of formula I having especially pronounced antibiotic activity.

Examples of such radicals $R_2$ are aminomethyl, 2-aminoprop-1-yl, carbamoyloxymethyl, 1-methyltetrazol-5-ylthiomethyl, 2-(1-tetrazolyl)propyl, 2-oxo-5-tetrahydrofurylmethyl, 2-oxo-5-pyrrolidylmethyl, 2-aminoethylthio, 2-formamidinoethylthio, 2-carbamoyloxyethylthio, 1-imidazolyl, 4,5-dimethyl-1-imidazolyl, 4-methyl-5-thiazolyl, 5-methyl-4-thiazolyl and 2-amino-4-methyl-5-thiazolyl, and the protected derivatives thereof.

The functional groups present in the compounds of formula I, i.e. hydroxy, carboxy, amino or sulfo groups, may be protected by customary protective groups $R_2^0$ and/or $R_3^0$. Customary protective groups are in particular those which may be used in penem, penicillin, cephalosporin and peptide chemistry. Such protective groups protect the functional groups in question from undesired elimination and substitution reactions and the like during the synthesis of the compound of the formula I from its precursors, and can be removed without damaging the penem ring structure.

Such protective groups can be removed readily, that is to say without the occurrence of undesirable secondary reactions, for example by solvolysis or reduction, or alternatively under physiological conditions.

Protective groups of this type and the methods by which they are introduced and removed are described, for example, in J. F. W. McOmie, "Protective Groups in Organic Chemistry", Plenum Press, London, New York, 1973, T. W. Greene, "Protective Groups in Organic Synthesis", Wiley, New York, 1981, "The Peptides", Vol. I, Schroeder und Luebke, Academic Press, London, New York, 1965 and Houben-Weyl, "Methoden der Organischen Chemie", Vol. 15/1, Georg Thieme Verlag, Stuttgart, 1974.

In compounds of formula I, a hydroxy group present in the radical $R_2$ may be protected e.g. by acyl radicals. Examples of suitable acyl radicals are lower alkanoyl, unsubstituted or substituted by halogen, for example acetyl or trifluoroacetyl, benzoyl, unsubstituted or substituted by nitro, e.g. benzoyl, 4-nitrobenzoyl or 2,4-dinitrobenzoyl, lower alkoxycarbonyl, unsubstituted or substituted by halogen, for example 2-bromoethoxycarbonyl or 2,2,2-trichloroethoxycarbonyl, lower alkenyloxycarbonyl, e.g. allyloxycarbonyl, aryl-lower alkenyloxycarbonyl, unsubstituted or substituted in the aryl ring, e.g. 3-phenylallyloxycarbonyl (cinnamyloxycarbonyl), wherein the aryl, i.e. phenyl, group may be substituted by one, two or more of e.g. lower alkoxy such as methoxy, halogen such as chlorine or fluorine, and/or nitro, or phenyl-lower alkoxycarbonyl, unsubstituted or substituted by nitro, for example 4-nitrobenzyloxycarbonyl. Further suitable hydroxy protective groups are e.g. trisubstituted silyl such as tri-lower alkylsilyl, e.g. trimethylsilyl or tert-butyldimethylsilyl, 2-halo-lower alkyl groups e.g. 2-chloro-, 2-bromo-, 2-iodo- and 2,2,2-trichloroethyl, and phenyl-lower alkyl, unsubstituted or substituted by halogen, e.g. chlorine, lower alkoxy, e.g. methoxy, and/or nitro e.g. corresponding benzyl. Tri-lower alkylsilyl, lower alkenyloxycarbonyl and halogen-substituted lower alkoxycarbonyl are preferred hydroxy protective groups.

A carboxy group present in the radical $R_2$, and also a carboxy group present in the 3-position of the penem ring or in the 1-position of the oxalic acid hemiester, is customarily protected in esterified form, the ester group being readily cleavable under mild conditions, for example under mildly reductive, such as hydrogenolytic, conditions, or under mildly solvolytic such as acidolytic or especially basic or neutral hydrolytic, conditions. A protected carboxy group can also be an esterified carboxy group that can readily be converted into a different functionally modified carboxy group, for example into a different esterified carboxy group.

Such esterified carboxy groups contain, as esterifying groups, preferably lower alkyl groups which are branched in the 1-position or suitably substituted in the 1- or 2-position. Preferred carboxy groups in esterified form, including also —COOR$_3^0$, are, inter alia, lower alkoxycarbonyl, for example methoxycarbonyl, ethoxycarbonyl, isopropoxycarbonyl or tert-butoxycarbonyl, and aryl or heteroarylmethoxycarbonyl having from 1 to 3 aryl radicals or having a monocyclic heteroaryl radical, which groups may be substituted by one or more of e.g. lower alkyl such as tert-lower alkyl, e.g. tert-butyl, halogen, e.g. chlorine, and/or nitro. Examples of such groups are benzyloxycarbonyl, unsubstituted or substituted e.g. as mentioned above, for example 4-nitrobenzyloxycarbonyl, diphenylmethoxycarbonyl or triphenylmethoxycarbonyl, unsubstituted or substituted e.g. as mentioned above, for example diphenylmethoxycarbonyl, or picolyloxycarbonyl, for example 4-picolyloxycarbonyl, or furfuryloxycarbonyl, such as 2-furfuryloxycarbonyl, each unsubstituted or substituted e.g. as mentioned above. Further suitable groups are lower alkanoylmethoxycarbonyl, such as acetonyloxycarbonyl, aroylmethoxycarbonyl in which the aroyl group is preferably benzoyl or benzoyl which is substituted e.g. by halogen such as bromine, for example phenacyloxycarbonyl, halo-lower alkoxycarbonyl such as 2-halo-lower alkoxycarbonyl, e.g. 2,2,2-trichloroethoxycarbonyl, 2-chloroethoxycarbonyl, 2-bromoethoxycarbonyl or 2-iodoethoxycarbonyl, or ω-halo-lower alkoxycarbonyl in which lower alkoxy contains from 4 to 7 carbon atoms, e.g. 4-chlorobutoxycarbonyl, phthalimidomethoxycarbonyl, lower alkenyloxycarbonyl, e.g. allyloxycarbonyl, aryl lower alkenyloxycarbonyl, unsubstituted or substituted in the aryl ring, e.g. 3-phenylalkyloxycarbonyl(cinnamyloxycarbonyl), in which the aryl, i.e. phenyl, ring may be substituted by e.g. one, two or more of lower alkoxy, such as methoxy, halogen, such as chlorine or fluorine, and/or nitro or ethoxycarbonyl substituted in the 2-position by lower alkylsulfonyl, cyano, or by tri-substituted silyl such as tri-lower alkylsilyl or triphenylsilyl, e.g. 2-methylsulfonylethoxycarbonyl, 2-cyanoethoxycarbonyl, 2-trimethylsilylethoxycarbonyl or 2-(di-n-butylmethylsilyl)ethoxycarbonyl.

A carboxyl protective group is also an esterified carboxyl group which can be cleaved under physiological conditions. It protects the compounds of formula I from salt formation in the gastro-intestinal tract in the case of oral administration, thus preventing premature excretion, and is in particular an acyloxymethoxycarbonyl group in which acyl is e.g. the radical of an organic carboxylic acid, preferably a lower alkanecarboxylic acid or arylcarboxylic acid, e.g. benzoic acid, which may be substituted e.g. by amino, or in which acyloxymethyl forms the radical of a lactone. Examples of such groups are lower alkanoyloxymethoxycarbonyl, amino-lower alkanoyloxymethoxycarbonyl, preferably α-amino-lower alkanoyloxymethoxycarbonyl, lower alkanoylaminomethoxycarbonyl, benzaminomethoxycarbonyl, 4-crotonolactonyl and 4-butyrolacton-4-yl. Further esterified carboxy groups $R_2$ that can be cleaved under physiological conditions are, for example, 5-indanyloxycarbonyl, 3-phthalidyloxycarbonyl, 1-lower alkoxycarbonyloxy-lower alkoxycarbonyl, 1-lower alkoxy-lower alkoxycarbonyl or 2-oxo-1,3-dioxolen-4-ylmethoxycarbonyl which is substituted in the 5-position of the dioxolene ring by lower alkyl or phenyl.

Other protected carboxy groups in esterified form are suitable organic silyloxycarbonyl groups, and also suitable organic stannyloxycarbonyl groups. In these groups, the silicon or tin atom preferably contains lower alkyl, preferably methyl or ethyl, or lower alkoxy, e.g. methoxy, as substituent(s). Suitable silyl and stannyl groups are in particular tri-lower alkylsilyl, preferably trimethylsilyl or dimethyl-tert-butylsilyl, or suitably substituted stannyl groups, e.g. tri-n-butylstannyl.

Preferred protected carboxy groups are the 4-nitrobenzyloxycarbonyl group, the lower alkenyloxycarbonyl, preferably allyloxycarbonyl, group, and the ethoxycarbonyl group which is substituted in the 2-position by lower alkylsulfonyl, cyano or tri-lower alkylsilyl, for example trimethylsilyl or di-n-butylmethylsilyl.

A protected amino group can be e.g. in the form of a readily cleavable acylamino, acylimino, etherified mercaptoamino, silylamino or stannylamino group or in the form of an enamino, nitro or azido group.

In a suitable acylamino group, acyl is e.g. the acyl radical of an organic acid containing e.g. up to 18 carbon atoms, preferably an alkanecarboxylic acid which may be substituted e.g. by halogen or phenyl, or a benzoic acid which may be substituted e.g. by halogen, lower alkoxy or nitro, or of a carbonic acid hemiester. Examples of such acyl groups are lower alkanoyl such as formyl, acetyl or propionyl, halo-lower alkanoyl such as 2-haloacetyl, preferably 2-fluoro-, 2-bromo-, 2-iodo-, 2,2,2-trifluoro- or 2,2,2-trichloroacetyl, benzoyl or substituted benzoyl, e.g. benzoyl, halobenzoyl such as 4-chlorobenzoyl, lower alkoxybenzoyl such as 4-methoxybenzoyl, or nitrobenzoyl such as 4-nitrobenzoyl. Particularly suitable acyl groups are also lower alkenyloxycarbonyl, e.g. allyloxycarbonyl, aryl-lower alkenyloxycarbonyl, unsubstituted or substituted in the aryl ring, e.g. 3-phenylallyloxycarbonyl (cinnamyloxycarbonyl), wherein the aryl, i.e. phenyl, group may be substituted by one, two or more of e.g. lower alkoxy such as methoxy, halogen such as chlorine or fluorine, and/or nitro, or lower alkoxycarbonyl, unsubstituted or substituted in the 1- or 2-position, such as lower alkoxycarbonyl, e.g. methoxy- or ethoxycarbonyl, unsubstituted or substituted benzyloxycarbonyl, for example benzyloxycarbonyl or 4-nitrobenzyloxycarbonyl, aroylmethoxycarbonyl, in which the aroyl group is preferably benzoyl or benzoyl which is substituted e.g. by halogen such as bromine, for example phenacyloxycarbonyl, 2-halo-lower alkoxycarbonyl, e.g. 2,2,2-trichloroethoxycarbonyl, 2-chloroethoxycarbonyl, 2-bromoethoxycarbonyl or 2-iodoethoxycarbonyl, or 2-(tri-substituted silyl)ethoxycarbonyl such as 2-tri-lower alkylsilylethoxycarbonyl, e.g. 2-trimethylsilylethoxycarbonyl or 2-(di-n-butylmethylsilyl)ethoxycarbonyl, or 2-triarylsilylethoxycarbonyl such as 2-triphenylsilylethoxycarbonyl.

In an acylimino group acyl is e.g. the acyl radical of an organic dicarboxylic acid containing e.g. up to 12 carbon atoms, especially of a suitable aromatic dicarboxylic acid such as phthalic acid. Such a group is preferably phthalimino.

An etherified mercaptoamino group is preferably a phenylthioamino group which is unsubstituted or substituted by lower alkyl such as methyl or tert-butyl, lower alkoxy such as methoxy, halogen such as chlorine or bromine, and/or by nitro, or is a pyridylthioamino group. Corresponding groups are e.g. 2- or 4-nitrophenylthioamino or 2-pyridylthioamino.

A silyl- or stannylamino group is preferably an organic silyl- or stannylamino group in which the substituents of the silicon or tin atom are preferably lower alkyl, e.g. methyl, ethyl, n-butyl or tert-butyl, or lower alkoxy, e.g. methoxy. Particularly suitable silyl or stannyl groups are tri-lower alkylsilyl, preferably trimethylsilyl, and also dimethyl tert-butylsilyl, or suitably substituted stannyl, e.g. tri-n-butylstannyl.

Further protected amino groups are e.g. enamino groups that contain an electrophilic substituent, e.g. a carbonyl group, at the double bond in the 2-position. Protective groups of this type are e.g. 1-acyl-lower alk-1-en-2-yl radicals in which acyl is e.g. the corresponding radical of a lower alkanecarboxylic acid, for example acetic acid, of a benzoic acid which may be substituted e.g. by lower alkyl such as methyl or tert-butyl, lower alkoxy such as methoxy, halogen such as chlorine, and/or by nitro, or preferably of a carbonic acid hemiester such as a carbonic acid lower alkyl hemiester, e.g. a carbonic acid methyl hemiester or ethyl hemiester, and in which lower alk-1-ene is preferably 1-propene. Suitable protective groups are preferably 1-lower alkanoylprop-1-en-2-yl, for example 1-acetylprop-1-en-2-yl, or 1-lower alkoxycarbonylprop-1-en-2-yl, e.g. 1-ethoxycarbonylprop-1-en-2-yl.

Preferred protected amino groups are e.g. azido, phthalimido, nitro, lower alkenyloxycarbonylamino, e.g. allyloxycarbonylamino, and unsubstituted or nitro-substituted benzyloxycarbonylamino.

Surprisingly, the use of cinnamyloxycarbonyl as protective group in compounds wherein $R_2$ is a protected aminomethyl group results in crystalline intermediates of formulae I, IV, VII and VIII.

A protected sulfo group in the radical $R_2$ is preferably an esterified sulfo group such as a sulfo group esterified by an aliphatic, cycloaliphatic, cycloaliphatic-aliphatic, aromatic or araliphatic alcohol, for example a lower alkanol, or by a silyl or stannyl radical such as tri-lower alkylsilyl. In a sulfo group, the hydroxy group may be etherified e.g. in the same manner as the hydroxy group in an esterified carboxy group.

The significance of $R_3^0$ as a carboxyl protective group may be inferred from the protected carboxyl groups as defined above.

W in a compound of formula II is defined in process (a).

Salts of compounds of the invention are preferably pharmaceutically acceptable, non-toxic salts of compounds of formula I. Such salts are formed e.g. from the acid groups present in compounds of formula I, for example carboxy and sulfo groups, and are in particular metal or ammonium salts such as alkali metal and alkaline earth metal salts, for example sodium, potassium, magnesium or calcium salts, and ammonium salts with ammonia or suitable organic amines such as lower alkylamines, e.g. triethylamine, hydroxy-lower alkylamines, e.g. 2-hydroxyethylamine, bis(2-hydroxyethyl)amine or tris(2-hydroxyethyl)amine, basic aliphatic esters of carboxylic acids, e.g. 2-diethylaminoethyl 4-aminobenzoate, lower alkylene-amines, e.g. 1-ethylpiperidine, cycloalkylamines, e.g. dicyclohexylamine, or benzylamines, e.g. N,N'-dibenzylethylenediamine, dibenzylamine or N-benzyl-β-phenethylamine. Compounds of formula I containing a basic group, for example having an amino group, can form acid addition salts, for example with inorganic acids such as hydrochloric acid, sulfuric acid or phosphoric acid, or with suitable organic carboxylic or sulfonic acids, e.g. acetic acid, succinic acid, fumaric acid, maleic acid, tartaric acid, oxalic acid, citric acid, benzoic acid, mandelic acid, malic acid, ascorbic acid, methanesulfonic acid or 4-toluenesulfonic acid. Compounds of formula I containing an acid group and a basic group can also be in the form of inner salts, i.e. in zwitterion form.

For isolation or purification it is also possible to use pharmaceutically unacceptable salts. Only the pharmaceutically acceptable, non-toxic, salts are used therapeutically and are therefore preferred.

The individual steps of the process of the present invention are carried out as follows.

Step (a): The starting compounds of formula II are known (e.g. from EP No. 82113, DE-OS Nos. 3 224 055, 3 013 997 or S. Hanessian et al., J. Am. Chem. Soc. 1985, 107, 1438–1439) or they can be prepared in a manner known per se. A group W which can be replaced by the group

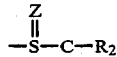

is a leaving group, e.g. an acyloxy group, wherein acyl is e.g. the radical of an organic carboxylic acid, e.g. lower alkanoyl such as acetyl or propionyl, benzoyl or benzoyl which is substituted by nitro, e.g. benzoyl, 4-nitrobenzoyl or 2,4-dinitrobenzyol, or phenyl-lower alkanoyl such as phenylacetyl, a sulfonyl radical $R_o$—$SO_2$—, wherein $R_o$ is an organic radical, e.g. lower alkyl or hydroxy-substituted lower alkyl, e.g. methyl, ethyl, tert-butyl, 2-hydroxyethyl, 1-hydroxyprop-2-yl or 1-hydroxy-2-methylprop-2-yl, benzyl, phenyl or phenyl which is substituted by lower alkyl or halogen, e.g. phenyl, 4-bromophenyl or 4-methylphenyl, a halogen atom, e.g. a bromine, iodine or, preferably, chlorine atom, or also azido. W is preferably acetoxy, benzoyloxy, methanesulfonyl, benzenesulfonyl, toluenesulfonyl, or chlorine.

The starting compounds of formula II may be used as cis- or transcompounds or as a mixture of cis-trans-compounds, i.e. the $C_4$ atom of the azetidine ring can have the R—, S— or R,S-configuration.

The compounds which introduce the radical of formula III are the corresponding thiocarboxylic acids H—S—C(=Z)—$R_2$ themselves or salts thereof, e.g. alkali metal salts such as the sodium or potassium salt.

The substitution can be carried out in an organic solvent, e.g. in a lower alkanol such as methanol or ethanol, a lower alkanone, e.g. acetone, a lower alkanecarboxamide, e.g. dimethylformamide, or in a similar inert solvent. The reaction is normally carried out at room temperature, but may also be conducted at elevated or low temperature, e.g. in the range from about 0° to 40° C.

The group which is introduced is directed by the radical $R_1$—CH(OH) exclusively to the trans-position.

Step (b): In the intermediates of formula IV, functional groups present in the radical $R_2$, e.g. carboxyl, amino or hydroxyl groups, are protected by a customary protective group.

An acylating agent which introduces the acyl radical of a carboxylic acid of formula V is either the carboxylic acid of formula V itself or a reactive functional derivative or a salt thereof. As it is desired to acylate the 1'-hydroxy group as well as the amino group, at least two equivalents of the acylating agent must be employed.

If a free acid of the formula V is used for the acylation, the reaction is generally carried out in the presence of a suitable condensation agent, e.g. a carbodiimide such as N,N'-diethylcarbodiimide, N,N'-dipropylcarbodiimide, N,N'-dicyclohexylcarbodiimide or N-ethyl-N'-3-dimethylaminopropylcarbodiimide, a suitable carbonyl compound, e.g. carbonyldiimidazole, or a 1,2-oxazolium compound such as 2-ethyl-5-phenyl-1,2-oxazolium-3'-sulfonate or 2-tert-butyl-5-methyl-1,2-oxazolium perchlorate, or a suitable acylamino compound, e.g. 2-ethoxy-1-ethoxycarbonyl-1,2-dihydroquinoline.

The condensation reaction is preferably carried out in an anhydrous reacton medium, preferably in an inert solvent, for example methylene chloride, dimethylformamide, acetonitrile or tetrahydrofuran, if desired or necessary with cooling or heating, e.g. in the temperature range from about −40° C. to +100° C., preferably from about −20° C. to +50° C., and, if necessary, in an inert gas atmosphere, e.g. in a nitrogen atmosphere.

A reactive, i.e. carboxamide-forming, functional derivative of a carboxylic acid of formula V is preferably an anhydride, preferably a mixed anhydride, of an inorganic acid, e.g. a hydrohalic acid, and is e.g. the corresponding carboxylic acid halide, for example the carboxylic acid bromide or preferably the carboxylic acid chloride, and also the carboxylic acid azide. Further inorganic acids that are suitable for the formation of mixed anhydrides are phosphorus-containing acids, e.g. phosphoric acid, diethylphosphoric acid or phosphorous acid, sulfur-containing acids, e.g. sulfuric acid, or hydrocyanic acid. A reactive functional derivative of a carboxylic acid of formula V is also formed by condensation with an organic carboxylic acid, e.g. with a lower alkanecarboxylic acid which is unsubstituted or substituted by halogen, e.g. fluorine or chlorine, or by cyano, for example pivalic acid, isovaleric acid, trifluoroacetic acid or cyanoacetic acid, with a lower alkyl hemiester of carbonic acid, e.g. the ethyl or isobutyl hemiester of carbonic acid, or with an organic, e.g. aliphatic or aromatic, sulfonic acid such as methanesulfonic acid or p-toluenesulfonic acid.

A reactive functional derivative of a carboxylic acid of formula V is also an activated ester with a vinylogous alcohol, i.e. with an enol, e.g. a vinylogous lower alkenol, an iminomethyl ester halide, for example dimethyliminomethyl ester chloride, obtained from the carboxylic acid of formula V, and, for example, dimethyl-(1-chloroethylidene)-iminium chloride of formula $[(CH_3)_2N^{\ominus}=C(Cl)CH_3]Cl^{\ominus}$ which, in turn, can be obtained e.g. from N,N-dimethylacetamide and phosgene or oxalyl chloride, an aryl ester, e.g. a phenyl ester substituted by halogen, e.g. chlorine, and/or by nitro, for example a pentachlorophenyl, 4-nitrophenyl or 2,4-dinitrophenyl ester, an N-heteroaromatic ester, e.g. N-benzotriazole ester, or an N-diacylimino ester, e.g. an N-succinimino or N-phthalimino ester.

Preferred acylating agents are the acid halides, e.g. the chlorides, most preferably allyl oxalate chloride.

The acylation with a reactive functional derivative of the carboxylic acid of formula V, preferably an acid halide, is preferably carried out in the presence of a suitable acid acceptor, for example a suitable organic base. A suitable organic base is e.g. an amine, e.g. a tertiary amine such as tri-lower alkylamine, e.g. trimethylamine, triethylamine or ethyldiisopropylamine, or an N,N-di-lower alkylaniline, e.g. N,N-dimethylaniline, or a cyclic tertiary amine, e.g. an N-lower alkylated morpholine, for example N-methylmorpholine, or is e.g. a base of the pyridine type, for example pyridine. A suitable acid acceptor is also an inorganic base, for example a hydroxide, carbonate or bicarbonate of an alkali metal or alkaline earth metal, for example sodium, potassium or calcium hydroxide, sodium potassium or calcium carbonate or sodium potassium or calcium bicarbonate.

The acylation with a reactive functional derivative of the carboxylic acid of formula V is preferably carried out in an inert, preferably anhydrous, solvent or mixture of solvents, for example in a carboxamide such as a formamide, e.g. dimethylformamide, a halogenated hydrocarbon such as methylene chloride, carbon tetrachloride or chlorobenzene, a ketone such as acetone, a cyclic ether such as tetrahydrofuran, an ester such as ethyl acetate, or a nitrile such as acetonitrile, or in a mixture thereof, if necessary or desired at reduced or elevated temperature, e.g. in a temperature range from about $-40°$ C. to $+100°$ C., preferably from about $-10°$ C. to $+50°$ C., and, if necessary, in an inert gas atmosphere, e.g. in a nitrogen atmosphere.

A reactive functional derivative of an acid of the formula V to be used in the acylation reaction can be formed in situ.

Step (c): An organic compound of trivalent phosphorus is derived e.g. from phosphorous acid and is preferably an ester thereof with a lower alkanol, e.g. methanol or ethanol, and/or with an unsubstituted or substituted aromatic hydroxy compound, e.g. phenol or pyrocatechol, or is an amide ester thereof of formula $P(OR_a)-N(R_b)_2$, wherein $R_a$ and $R_b$ are each independently of the other lower alkyl, e.g. methyl, or aryl, e.g. phenyl. Preferred compounds of trivalent phosphorus are tri-lower alkylphosphites, e.g trimethylphosphite, triethylphosphite or triisopropylphosphite.

The reaction is preferably carried out in an inert solvent such as an aromatic hydrocarbon, e.g. benzene or toluene, an ether, e.g. dioxane or tetrahydrofuran, or in a halogenated hydrocarbon, e.g. methylene chloride or chloroform, in the temperature range from about 20° to 80° C., preferably from about 40° to 60° C., with 1 molar equivalent of a compound of formula VI being reacted with 2 molar equivalsnts of the phosphorus compound. The preferred procedure is to charge the compound of formula VII in an inert solvent to the reactor and to add the phosphorus compound dropwise, preferably dissolved in the same inert solvent, over a substantial period of time, for example over 2 to 4 hours, and to heat the reaction mixture to about 100°–110° C. until the reaction is complete.

In a preferred embodiment of the process, the starting material of formula VII is prepared as indicated above and, without being isolated from the reaction mixture, reacted with the organic compound of trivalent phosphorus.

Step (d): In a resultant compound of formula VIII, the protective groups $R_3^o$, $R_3^oO—CO—CO$ and any protective groups $R_2^o$ present in the radical $R_2$, e.g. protected carboxyl, hydroxyl, amino and/or sulfo groups, can be removed in a manner known per se, e.g. by solvolysis, preferably hydrolysis, alcoholysis or acidolysis, or by reduction, preferably hydrogenolysis or chemical reduction, if desired stepwise and in any order or simultaneously, and replaced by hydrogen.

Thus the oxalyl ester group $—CO—COO—R_3^o$ may be removed stepwise and/or selectively, i.e. retaining the protective group $R_3^o$ at the 4-carboxyl group or other protective groupa $R_2^o$, and replaced by hydrogen.

The removal is effected for example under alcoholic conditions, e.g. in the presence of an alkali metal hydroxide such as lithium, sodium or potassium hydroxide, or a corresponding carbonate or, preferably, bicarbonate, which is employed preferably in catalytic or up to equivalent amount. A suitable solvent is a mixture of water with a water-soluble organic solvent such as a lower alkanol, e.g. methanol, ethanol or isopropanol, a lower ketone, e.g. acetone, a lower cyclic ether, e.g. dioxane or tetrahydrofuran, a lower nitrile, e.g. acetonitrile, a lower amide, e.g. dimethylformamide, or a lower sulfoxide, e.g. dimethylsulfoxide, and the like. For the optional selective removal of the 1'-oxalyl protective group, saponification is preferably carried out in aqueous methanol (c. 80%) in the presence of sodium bicarbonate.

The temperatures are in the range from setting point to the boiling point of the solvent employed, i.e. from about $-20°$ to $+100°$ C. It is generally preferable to carry out the reaction at low temperature, i.e. in the range from 0° to 20° C., most preferably at about 0° C.

It is also possible to remove first a $R_3^o$ group by a method described below, following which the resultant 1'-oxalic acid hemiester is completely saponified under the alkaline conditions described above.

A protected carboxyl group, e.g. a $—COO—R_3^o$ group, can be freed in a manner known per se. For example, tert-lower alkoxycarbonyl, or lower alkoxycarbonyl substituted in the 2-position by a tri-substituted silyl group or in the 1-position by lower alkoxy, or unsubstituted or substituted diphenylmethoxycarbonyl can be converted into free carboxy, e.g. by treatment with a carboxylic acid such as formic acid or trifluoroacetic acid, with the optional addition of a nucleophilic compound such as phenol or anisole. Unsubstituted or substituted benzyloxycarbonyl can be cleaved e.g. by hydrogenolysis, i.e. by treatment with hydrogen in the presence of a metallic hydrogenation catalyst such as a palladium catalyst. It is also possible to convert suitably substituted benzyloxycarbonyl such as 4-nitrobenzyloxycarbonyl into free carboxy by means of chemical reduction, for example by treatment with an alkali metal dithionite, e.g. sodium dithionite, or with a reducing metal such as tin, or with a reducing metal salt such as a chromium(II) salt, e.g. chromium(II) chloride, usually in the presence of a hydrogen donor which, together with the metal, is capable of producing nascent hydrogen, for example a suitable carboxyiic acid such as a lower alkanecarboxylic acid which is unsubstituted or substituted e.g. by hydroxy, for example acetic acid, formic acid or glycolic acid, or an alcohol or thiol, preferably with the addition of water. The removal of an allyl protecting group can be effected e.g. by reaction with a palladium compound, for example tetrakis(triphenylphosphine)palladium, in the presence of an allyl group acceptor such as acetyl acetone or, preferably, dimedone, and optionally of triphenylphosphine and with the addition of a carboxylic acid, for example 2-ethylhexanoic acid, or a salt thereof. By treatment with a reducing metal or metal salt, as described above, it is also possible to convert 2-halo-lower alkoxycarbonyl (optionally after converting a 2-bromo-lower alkoxycarbonyl group into a corresponding 2-iodo-lower alkoxycarbonyl group) or aroylmethoxycarbonyl into free carboxy, while aroylmethoxycarbonyl can also be cleaved by treatment with a nucleophilic, preferably salt-forming, reagent such as sodium thiophenolate or sodium iodide. Substituted 2-silylethoxycarbonyl can be converted into free carboxy also by treatment with a salt of hydrofluoric acid which donates the fluoride anion, for example an alkali metal fluoride such as sodium fluoride, in the presence of a macrocyclic polyether ("crown ether") or with a fluoride of an organic quaternary base such as tetra-lower alkylammonium fluoride, for example tetrabutylammonium fluoride. Carboxy esterified by an organic silyl or stannyl group, such as tri-lower alkylsilyl or tri-lower alkylstannyl, can be freed in customary manner by solvolysis, for example by treatment with water or an alcohol. A lower alkoxycarbonyl group substituted in the 2-position by lower alkylsulfonyl or cyano can be converted into free carboxy, e.g. by treatment with a base such as an alkali metal hydroxide or alkaline earth metal hydroxide or an alkali metal carbonate or alkaline earth metal carbonate, for example sodium or potassium hydroxide or sodium or potassium carbonate.

In compounds of formula VIII, wherein the radical $R_2$ contains protected hydroxy as substituent, the protected hydroxy group can be converted in a manner known per se into the free hydroxy group. For example, a hydroxy group protected by a suitable acyl group or by an organic silyl or stannyl group is freed in the same manner as a correspondingly protected amino group (see below). A tri-lower alkylsilyl group can also be removed e.g. with tetrabutylammonium fluoride and acetic acid (under these conditions, carboxy groups protected by trisubstituted silylethoxy are not cleaved). A 2-halo-lower alkyl group and an unsubstituted or substituted benzyl group are removed by reduction.

In a compound of formula VIII containing a protected amino group, said group may be converted into the free amino group in a manner known per se, e.g. preferably by means of solvolysis or reduction, depending on the nature of the protective group. For example, 2-halo-lower alkoxycarbonylamino (optionally after converting a 2-bromo-lower alkoxycarbonylamino group into a 2-iodo-lower alkoxycarbonylamino group), aroylmethoxycarbonylamino or 4-nitrobenzyloxycarbonylamino can be cleaved by treatment with a suitable chemical reducing agent such as zinc, in the presence of a suitable carboxylic acid such as aqueous acetic acid, or by catalysis with hydrogen in the presence of a palladium catalyst. Aroylmethoxycarbonylamino may be cleaved also by treatment with a nucleophilic, preferably salt-forming, reagent such as sodium thiophenolate, and 4-nitrobenzyloxycarbonylamino may also be cleaved by treatment with an alkali metal dithionite such as sodium dithionite. Unsubstituted or substituted benzyloxycarbonylamino may be cleaved e.g. by hydrogenolysis, i.e. by treatment with hydrogen in the presence of a suitable hydrogenation catalyst such as a palladium catalyst, and allyloxycarbonylamino may be cleaved e.g. by reaction with a palladium compound such as tetrakis(triphenylphosphine)palladium, in the presence of an allyl group acceptor such as acetyl acetone or, preferably, dimedone, and optionally of triphenylphosphine and by treatment with a carboxylic acid, e.g. 2-ethylhexanoic acid, or with a salt thereof. An amino group protected by an organic silyl or stannyl group can be freed e.g. by hydrolysis or alcoholysis, and an amino group protected by 2-halo-lower alkanoyl, for example 2-chloroacetyl, can be freed by treatment with thiourea in the presence of a base or with a thiolate salt such as an alkali metal thiolate, or with thiourea, and subsequent solvolysis, such as alcoholysis or hydrolysis, of the resultant condensation product. An amino group protected by 2-substituted silylethoxycarbonyl can be converted into the free amino group by treatment with a salt of hydrofluoric acid which donates the fluoride anion, for example an alkali metal fluoride such as sodium fluoride, in the presence of a macrocyclic polyether ("crown ether") or with a fluoride of an organic quaternary base such as tetra-lower alkylammonium fluoride, e.g. tetraethylammonium fluoride. An amino group protected in the form of an azido or nitro group is converted into free amino e.g. by reduction, for example by catalytic hydrogenation with hydrogen in the presence of a hydrogenation catalyst such as platinum oxide, palladium or Raney nickel, or by treatment with zinc in the presence of an acid such as acetic acid. An amino group protected in the form of a phthalimido group can be converted into the free amino group by reaction with hydrazine. Further, an arylthioamino group can be converted into amino by treatment with a nucleophilic reagent such as sulphurous acid.

A protected, in particular esterified, sulfo group is freed in the same manner as a protected carboxy group.

Salts of compounds of formula I containing salt-forming groups may be prepared in a manner known per se. Thus salts of compounds of formula I containing a free carboxy or sulfo group can be formed e.g. by treatment with a metal compound such as an alkali metal salt of a suitable organic carboxylic acids, for example the sodium salt of α-ethylcaproic acid, or with inorganic alkali metal or alkaline earth metal salts, for example sodium bicarbonate, or with ammonia or with a suitable organic amine, preferably using stoichiometric amounts or only a small excess of the salt-forming agent. Acid addition salts of compounds of formula I are obtained in customary manner, for example by treatment with a suitable acid or a suitable anion exchange reagent. Inner salts of compounds of formula I can be formed e.g. by neutralising salts, such as acid addition salts, to the isoelectric point, e.g. with a weak base, or by treatment with an ion exchanger.

Salts can be converted into the free compounds in customary manner; metal and ammonium salts, for example by treatment with suitable acids, and acid addition salts, for example by treatment with a suitalie base.

In all subsequent conversions of resultant compounds of formula I, those reactions are preferred which take place under weakly alkaline or preferably neutral conditions.

The process also includes those embodiments in which compounds obtained as intermediates are used as starting materials and the remaining process steps are carried out therewith, or the process is discontinued at any stage, as well as the individual process steps (a) to (d). Further, starting materials can be used in the form of derivatives or can be prepared in situ, optionally under the reaction conditions.

The invention also relates to the novel compounds of formulae I, IV, VII and VIII.

Novel compounds of formula I are in particular those wherein $R_2$ is cinnamyloxycarbonylaminomethyl and $R_1$ and $R_3$ have the given meanings, with the preferred meaning of $R_1$ being methyl and that of $R_3$ allyl.

Novel compounds of formula IV are in particular those wherein $R_2$ is cinnamyloxycarbonylaminomethyl and $R_1$ and Z have the given, in particular preferred, meanings.

In the novel compounds of formulae VII and VIII, $R_2$ and $R_3^o$ have the given, in particular preferred, meanings.

Particularly preferred compounds of formulae I, IV, VII and VIII are those in crystalline form, wherein $R_2$ is cinnamyloxycarbonylaminomethyl.

The invention is illustrated by the following Examples.

The following abbreviations are used in the Examples:
TLC: thin-layer chromatogram
IR: infra-red spectrum
UV: ultra-violet spectrum

EXAMPLE 1

(3S,4R,1'R)-3-(1'-hydroxyethyl)-4-(N-allyloxycarbonylglycylthio)-2-azetidinone (a) A solution of 14.2 g (40 mmols) of N-allyloxycarbonylthioglycine dicyclohexylammonium salt in 60 ml of water and 40 ml of 1N aqueous NaOH is extracted with three 20 ml portions of methylene chloride and the aqueous phase is adjusted to pH 7–8 with about 1 ml of 0.1N aqueous HCl. The resultant aqueous thiolic acid solution is added at 30° C. over 5 minutes to a solution of 4.70 g (20 mmols) of (3R,4R,1'R)-3-(1'-hydroxyethyl)-4-benzoyloxy-2-azetidinone in 100 ml of acetonitrile. Then 2 ml of 0.1N aqueous NaOH are added at 25° C. and the batch is stirred for 30–35 minutes at 25° C. For working up, 250 ml of ethyl acetate and 30 g of NaCl are charged to a separating funnel and then the reaction mixture is added. After thorough shaking and separation of the aqueous phase, the organic phase is washed once with 50 ml of a 5% aqueous NaHCO$_3$ solution and twice with 50 ml of brine and dried over sodium sulfate. The solvent is removed in a rotary evaporator. The title compound is obtained in the form of an amorphous powder. The crude product can be purified by chromatography on silica gel (2:3 mixture of toluene/ethyl acetate). Rf value=0.23 (Merck plates, toluene/ethyl acetate (1:4); development with ninhydrin).

The same compound can also be obtained as follows:

(b) A solution of 85.2 g (239 mmols) of N-allyloxycarbonylthioglycine dicyclohexylammonium salt in 360 ml of water and 240 ml of 1N aqueous NaOH is extracted with three 40 ml portions of methylene chloride and the aqueous phase is adjusted to pH 7–8 with about 0.5 ml of 1N aqueous HCl. The resultant aqueous thiolic acid solution is added at 28° C. over 5 minutes to a solution of 30.1 g (128 mmols) of (3S,4R,1'R)-3-(1'-hydroxyethyl)-4-tert-butylsulfonyl-2-azetidinone in 300 ml of acetonitrile and 20 ml of H$_2$O. Then 12 ml of 0.1N aqueous NaOH are added at 25° C. and the batch is stirred for 30 minutes at 25° C. For working up, 700 ml of ethyl acetate and 90 g of NaCl are charged to a separating funnel and then the reaction mixture is added. After thorough shaking and separation of the organic phase, the organic phase is washed once with 100 ml of a 5% aqueous solution of NaHCO$_3$ and twice with 100 ml of a concentrated solution of sodium chloride and dried over sodium sulfate. The solvent is completely removed in a rotary evaporator. Then 100 ml of CH$_2$Cl$_2$ are added to the partly crystalline residue and the crystalline, unreacted educt is isolated by filtration and dried. The filtrate is concentrated by evaporation and purified by chromatography over 300 g of silica gel with toluene/ethyl acetate (4:6) The title compound so obtained has an Rf value of 0.23 (Merck plates, toluene/ethyl acetate (4:1); development with ninhydrin).

(c) A solution of 426 g (1.2 mmols) of N-allyloxycarbonylthioglycine dicyclohexylammonium salt in 1.2 ml of 1N aqueous NaOH is extracted with three 1.5 ml portions of methylene chloride and the aqueous phase is adjusted to pH 8–9 with 0.1N aqueous HCl. The resultant aqueous thiolic acid solution is added at 25° C. to a solution of 173.2 mg (1 mmol) of (3R,4R,1'R)-3-(1'-hydroxyethyl)-4-acetoxy-2-azetidinone in 1.7 ml of acetonitrile. Then 0.1 ml of 0.1N aqueous NaOH are added and the batch is stirred for 35 minutes at 21°–23° C. Working up is effected as in Example 1(a). The title compound is obtained after purifying the crude product by chromatography (2:3 mixture of toluene/ethyl acetate).

EXAMPLE 2

Allyl (5R,6S,1'R)-(1'-hydroxyethyl)-2-allyloxycarbonylaminomethylpenem-3-carboxylate To a solution of 2.88 g (10.0 mmols) of (3S,4R,1'R)-3-(1'-hydroxyethyl)-4-(N-allyloxycarbonylglycylthio)-2-azetidinone (crude product of process 1a) in 80 ml of methylene chloride (freshly filtered over Alox) are added in succession at −10° to −15° C., with stirring and excluding moisture, 3.86 ml (31.5 mmols) of freshly distilled allyl oxalyl chloride and 7.69 ml (44.8 mmols) of N-ethyldiisopropylamine, and stirring is continued for 30 minutes at −10° C. An IR sample shows the characteristic oxalimide-carbonyl absorption at 1820 cm$^{-1}$.

For working up, the reaction mixture is diluted with 50 ml of CH$_2$Cl$_2$ and washed three times with ice-cold water and once with ice-water and with 5 ml of saturated aqueous NaHCO$_3$ solution. The aqueous phases are extracted once with CH$_2$Cl$_2$. The combined organic phases are dried over Na$_2$SO$_4$, concentrated by evaporation under vacuum, and the crude product is dried under a high vacuum. The viscous residue containing the allyl (3S,4R,1'R)-2-[4-(N-allyloxycarbonylglycylthio)-3-(1'-allyloxyoxalyloxyethyl)-2-oxo-1-azetidinyl]-2-oxoacetate [IR(CH$_2$Cl$_2$) 3440 (NH); 1820

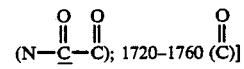

is dissolved in 30 ml of dioxane and the solution is treated at room temperature under nitrogen with 7 ml (40.2 mmols) of triethylphosphite. After 15 hours at room temperature, no more oxalimide can be detected in the IR spectrum (bands at 1820 cm$^{-1}$). The reaction mixture is concentrated by evaporation under vacuum, the residue is washed with 3×2 ml portions of toluene and 3×2 ml of decane, and each of the separating agents for removing excess phosphite/phosphate is stripped off under a high vacuum. The crude phosphorane is dissolved in 250 ml of dioxane for cyclisation and stirred for 5 hours at 105°–110° C. The reaction mixture containing the allyl (5R,6S,1'R)-2-allyloxycarbonylaminomethyl-6-[1'-(allyloxyoxalyloxy)ethyl]-2-penem-3-carboxylate [for analysis, a sample of the crude cyclisation product is purified on silica gel with a 4:1 mixture of toluene/ethyl acetate: UV (EtOH) 315 nm; IR(CH$_2$Cl$_2$) 3440 (NH); 1790, 1770, 1745, 1720

is concentrated by evaporation under vacuum to about 15 ml, and then 100 ml of methanol/H$_2$O (8:2) and 25 ml of a saturated aqueous NaHCO$_3$ solution are added at 0° C. After 20 minutes, the reaction mixture is poured into 300 ml of ethyl acetate and 50 ml of H$_2$O. The organic phase is separated and the aqueous phase is again extracted with 100 ml of ethyl acetate. The combined organic phases are dried over Na$_2$SO$_4$ and concentrated under vacuum to a volume of about 50 ml. The residue is diluted with 200 ml of methylene chloride, dried over Na$_2$SO$_4$, and concentrated completely under vacuum. The residue is chromatographed on 80 g of silica gel with toluene/ethyl acetate (3:2). The title compound is obtained after crystallisation from ether/hexane (3:7). Melting point: 141°–141.5° C.; Rf value=0.20 [Merck plates, toluene/ethyl acetate (1:1)].

EXAMPLE 3

(5R,6S,1'R)-2-aminomethyl-6-(1'-hydroxyethyl)-2-penem-3-carboxylic acid

A solution of 313 mg (0.85 mmols) of allyl (5R,6R,1'R)-2-allyloxycarbonylaminomethyl-6-(1'-hydroxyethyl)-2-penem-3-carboxylate and 174.6 mg (1.24 mmols) of dimedone in 7.5 ml of tetrahydrofuran is flushed with argon for 5 minutes and then 27 mg (0.023 mmols) of tetrakis(triphenylphosphine)palladium are added at room temperature under argon. A precipitate begins to form after c. 5 minutes and is isolated by filtration after stirring for another 2 hours, washed with c. 10 ml of tetrahydrofuran, and then dissolved in 4 ml of H$_2$O. A trace of activated carbon is added with a microspatula to the beige-coloured solution, followed by the addition of 2 trace amounts of Tonsil (fuller's earth). The mixture is then well stirred for 5 minutes, filtered over Hyflo, and concentrated under a high vacuum. The dense crystal slurry is diluted with 3 ml of cold ethanol and filtered with suction. The colourless crystals are washed with 2 ml of tetrahydrofuran and dried under a high vacuum. The title compound has an Rf value=0.50 [TLC: H$_2$O, OPTI UPC$_{12}$); $[\alpha]_D^{20}$ = +176 (c=0.5 in H$_2$O).

EXAMPLE 4

(3S,4R,1'R)-3-(1'-hydroxyethyl)-4-(N-cinnamyloxycarbonylglycylthio)-2-azetidinone (a) A solution of 301.8 mg (1.2 mmols) of N-cinnamyloxycarbonylthioglycine in 1.2 ml of 1N aqueous NaOH is adjusted to pH 8 with 0.1N aqueous HCl and added at 25° C. to 235 mg (1 mmol) of (3R,4R,1'R)-(1'-hydroxyethyl)-4-benzoyloxy-2-azetidinone in 2 ml of acetonitrile. 0.1 ml of 0.1N aqueous NaOH solution are added and the reaction mixture is stirred for 25 minutes at 25°–26° C.

For working up, the reaction mixture is extracted with 20 ml of ethyl acetate and 10 ml of brine. The organic phase is washed with 5 ml of a 5% aqueous solution of NaHCO$_3$ and twice with 5 ml of brine, dried over sodium sulfate and freed from solvent in a rotary evaporator. The residue is dissolved in 20 ml of toluene/ethyl acetate (2:3), stirred for 15 minutes with 1 g of silica gel and filtered over a G 2 glass frit, and concentrated. The title compound is obtained in the form of an amorphous powder. The crystalline title compound of m.p. 100°–101° C. is obtained from methylene chloride/diisopropyl ether (c. 1:1).

The same compound can also be obtained as follows:

(b) Following the procedure of process (a), starting from 173 mg (1 mmol) of (3R,4R,1'R)-3-(1'-hydroxyethyl)-4-acetoxy-2-azetidinone and chromatographing the crude product [silica gel, toluene/ethyl acetate (2:3)].

(c) Following the procedure of process a), starting from 235 mg (1 mmol) of (3S,4R,1'R)-3-(1'-hydroxyethyl)-4-tert-butylsulfonyl-2-azetidinone and chromatographing the crude product [silica gel, toluene/ethyl acetate (2:3)].

The starting N-cinnamyloxycarbonylthioglycine can be prepared as follows:

A solution of 13.4 g (100 mmols) of cinnamyl alcohol in 25 ml of toluene is added dropwise at 0° C. over 15 minutes to a solution of 78 ml of a 20% solution of phosgene in toluene. The reddish brown emulsion is warmed to room temperature while blowing in nitrogen, and stirred for 2 hours. The toluene is stripped off under vacuum (0.1 torr) and the residue is added at 0° C. to a solution of 3.75 g (50 mmols) of glycin, 12 ml of water and 6.07 ml of 30% aqueous NaOH solution. Then a further 6.07 ml of 30% aqueous NaOH solution are added dropwise at 5°–15° C. over 10 minutes. The reaction mixture is stirred for 2 hours (pH 12) and then poured into 70 ml of ethyl acetate and 70 ml of water. The aqueous phasa is separated, washed with 20 ml of ethyl acetate, adjusted to pH 1–2 with 2N aqueous HCl, and the precipitated N-cinnamyloxycarbonylglycine is extracted with a total amount of 120 ml of ethyl acetate. The combined organic phases are washed once with 10 ml of brine, dried over Na$_2$SO$_4$, and freed from solvent in a rotary evaporator. The title compound is crystallised from 50 ml of ethyl acetate and 25 ml of hexane. Melting point: 129°–130° C.

To a suspension of 7.81 g (33.2 mmols) of N-cinnamyloxycarbonylglycine in 66 ml of ethyl acetate are added 4.76 ml (36.4 mmols) of isobutyl chloroformate at −10° to −15° C., followed by the dropwise addition, at the same temperature, of 4 ml (36.3 mmols) of N-methylmorpholine. The reaction mixture is stirred for 1 hour at −10° to −15° C. A further 4 ml (36.3 mmols) of N-methylmorpholine are added dropwise over 30 minutes while simultaneously introducing gaseous hydrogen sulfide. When the addition of hydrogen sulfide is complete, a weak stream of nitrogen is introduced, with stirring, at −10° to −15° C. over 1 hour. Then 23.2 ml of 2N aqueous HCl are added dropwise, whereupon the temperature rises to ~0° C., and nitrogen is blown in over a further 30 minutes. The reaction mixture is then poured into 300 ml of ethyl acetate and the aqueous phase (pH 12) is separated and extracted in turn with ethyl acetate. The combined organic phases are washed twice with 20 ml of brine, dried over Na$_2$SO$_4$, and freed from solvent in a rotary evaporator. Recrystallisation of the crude product from ether/hexane at 0° C. gives the analytically pure title compound with a melting point of 67°–69° C.

EXAMPLE 5

Allyl (5R,6S,1′R)-6-(1′-hydroxyethyl)-2-cinnamyloxycarbonylaminomethylpenem-3-carboxylate To a solution of 310 mg (0.852 mmol) of (3S,4R,1′R)-3-(1′-hydroxyethyl)-4-(N-cinnamyloxycarbonylglycylthio)-2-azetidinone (crude product of Example 4) in 3.2 ml of methylene chloride are added in succession at −10° to −15° C., with stirring and excluding moisture, 0.216 ml (1.75 mmols) of freshly distilled allyl oxalyl chloride and 0.301 ml (1.75 mmols) of N-ethyldiisopropylamine, and stirring is continued for 30 minutes at −10° C. An IR sample (CH$_2$Cl$_2$) shows the characteristic oxalimide-carbonyl absorption at 1820 cm$^{-1}$.

For working up, the reaction mixture is diluted with 2 ml of CH$_2$Cl$_2$ and washed with two 4 ml portions of aqueous buffer solution. The aqueous phases are extracted once with CH$_2$Cl$_2$. The combined organic phases are dried over Na$_2$SO$_4$, concentrated by evaporation under vacuum, and the crude product is dried under a high vacuum. The resinous residue containing the allyl (3S,4R,1′R)-2-[4-(N-cinnamyloxycarbonylglycylthio)-3-(1′-allyloxyoxalyloxyethyl)-2-oxo-1-azetidinyl]-2-oxoacetate [IR (CH$_2$Cl$_2$) 3440 (NH); 1820

(N—C—C); 1750, 1725 (C)]

is dissolved in 0.37 ml of dioxane and the solution is treated at room temperature and under nitrogen with 0.51 ml (2.1 mmols) of triethylphosphite. After 15 hours at room temperature, no more oxalimide can be detected in the IR spectrum (bands at 1820 cm$^{-1}$). The reaction mixture is freed from excess phosphite/phosphate under vacuum (bulb tube; 0.1 torr). The residual crude phosphorane is dissolved in 3.3 ml of dioxane for cyclisation and stirred for 12 hours at 100° C. The reaction mixture containing the allyl (5R,6S,1′R)-2-cinnamyloxycarbonylaminomethyl-6-[1′-(allyloxyoxalyloxy)ethyl]-2-penem-3-carboxylate [for analysis, a sample of the crude cyclisation product is purified on silica gel with toluene/ethyl acetate (9:1): m.p. 87°–88° C., UV spectrum (EtOH)=315 nm. IR spectrum (in CH$_2$Cl$_2$)=3440 (NH), 1795, 1770, 1745,

1720, (C)]

is concentrated by evaporation at room temperature and the residue is dissolved in 4 ml of methanol. Then 2 ml of 5% aqueous NaHCO$_3$ solution are added dropwise at 0° C. and the precipitated title compound is isolated by filtration and recrystallised from methanol. Melting point: 178°–180° C.

EXAMPLE 6

(5R,6S,1′R)-2-aminomethyl-6-(1′-hydroxyethyl)-2-penem-3-carboxylic acid

A solution of 48 mg (0.108 mmol) of allyl (5R,6S,1′R)-6-(1′-hydroxyethyl)-2-cinnamyloxycarbonylaminomethyl-2-penem-3-carboxylate and 22.3 mg (0.159 mmols) of dimedome in 1 ml of tetrahydrofuran is flushed with nitrogen for 5 minutes and then 1.6 mg of tetrakis(triphenylphosphine)palladium are added at room temperature. The title compound begins to precipitate after about 30 minutes. After stirring for another 2½ hours, the product is isolated by filtration, thoroughly washed with tetrahydrofuran, and dried under a high vacuum to give the title compound with Rf=0.50 (TLC: H$_2$O, OPTI UPC$_{12}$); UV spectrum (in H$_2$O): 328 nm.

What is claimed is:

1. A compound of the formula

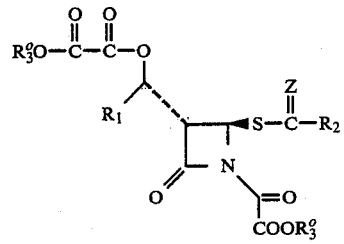

wherein

R$_1$ is hydrogen or lower alkyl;

R$_2$ is an organic radical consisting of up to 18 carbon atoms, up to 5 nitrogen atoms, up to 5 oxygen atoms, up to 3 sulfur atoms, up to 3 halogen atoms and a commensurate number of hydrogen atoms; selected from Group (I) consisting of lower alkyl-X-, lower alkenyl-X, cyclo-lower alkyl-X-, cylco-lower alkenyl-X-, aryl-X-, aryl-lower alkyl-X-, aryl-lower alkenyl-X-, heterocyclyl-X-, heterocyclyl-lower alkyl-X-, heterocyclyl-lower alkenyl-X-, heterocyclyl-X-lower alkyl and heterocyclyl-X-lower alkenyl, wherein each X is independently a bond, an oxygen atom or a sulfur atom;

each heterocyclyl group consisting of an aromatic monocyclic 5- to 6-membered heteroaryl radical selected from the group consisting of monoaza-, diaza-, triaza-, tetraza-, oxa-, oxaaza, oxadiaza-, oxatriaza-, monothia-, thiaza-, thiadiaza-, or thiatriazacyclic radical, a dihydro or tetrahydro radical thereof, and an unsaturated or partially saturated monobenzoo, dibenzo, pyrido, or pyrimido derivative of such 5- or 6-membered radical;

each of the aforesaid (I) being unsubstituted or substituted by up to three substituents which are the same or different such that the resultant substituted R$_2$ group consists of up to 18 carbon atoms, up to 5 nitrogen atoms, up to 5 oxygen atoms, up to 3 sulfur atoms, up to 3 halogen atoms and a commensurate number of hydrogen atoms;

each of said substituents being selected from:

(a) hydroxy, lower alkoxy, phenyl-lower alkoxy, lower alkanoyloxy, halogen, mercapto, lower alkylthio, and phenylthio;

(b) lower alkyl which is unsubstituted or substituted by hydroxy, lower alkoxy, carboxy, lower alkoxycarbonyl, carbamoyl, amino, lower alkylamino, di-lower alkylamino, lower alkyleneamino, lower alkanoylamino, mercapto, lower alkylthio, sulfo, or lower alkoxycarbonylamino, said lower alkoxycarbonylamino being unsubstituted or substituted by amino, by carboxy, or by both amino and carboxy;

(c) lower alkylene, unsubstutited or lower alkylated aza-lower alkylene, oxa-lower alkylene, di-oxa lower alkylene, and thia-lower alkylene;

(d) amino, lower alkylamino, di-lower alkylamino, lower alkyleneamino, guanidino, and carbamoylamino;

(e) lower alkanoylamino and lower alkoxycarbonylamino, each of which is unsubstituted or substituted by at least one substituent selected from amino and carboxy;

(f) carboxy, lower alkoxycarbonyl, carbamoyl, N-mono-lower alkylcarbamoyl, N,N-di-lower alkylcarbamoyl, cyano, sulfo, and sulfamoyl;

(g) phenyl which is unsubstituted or substituted by at least one substituent selected from lower alkyl, nitro, amino, hydroxy, lower alkoxy, carboxy, and halogen; and (h) cycloalkyl, nitro, oxo, and oxido; "lower", in each case indicating up to and including 7 carbon atoms;

$R_3^o$ is a conventional carboxyl protecting group; and

Z is oxygen or sulfur;

and when $R_2$ contains a functional group it is unprotected or has at least one of its functional groups protected by a conventional penem protecting moiety.

2. The compound of claim 1 wherein $R_2$ is selected from the group consisting of aminomethyl, 2-aminopropyl-carbamoyloxymethyl, 1-methyltetrazol-5-ylthiomethyl, 2-(1-tetrazolyl)-propyl, 2-oxo-5-tetrahydrofurylmethyl, 2-oxo-5-pyrrolidylmethyl, 2-aminoethylthio, 2-formamidinoethylthio, 2-carbamoyloxyethylthio, 1-imidazolyl, 4,5-dimethyl-1-imidazolyl, 4-methyl-5-thiazolyl, 5-methyl-4-thiazolyl, and 2-amino-4-methyl-5-thiazolyl;

which $R_2$ substituent is unprotected or has at least one of its functional groups protected by a conventional penem protecting moiety.

3. Allyl (3S,4R,1′R)-2-[4-(N-allyloxycarbonylglycylthio)-3-(1′-allyloxyoxalyloxyethyl)-2-oxo-1-azetidinyl]-2-oxoacetate according to claim 1.

4. Allyl (3S,4R,1′R)-2-[4-(N-cinnamyloxycarbonylglycylthio)-3-(1′-allyloxyoxalyloxyethyl)-2-oxo-1-azetidinyl]-2-oxoacetate according to claim 1.

5. A compound of the formula

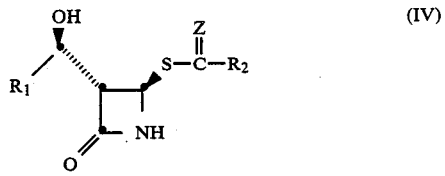

wherein $R_1$ is hydrogen or lower alkyl;

$R_2$ is cinnamyloxycarbonylaminomethyl; and

Z is oxygen or sulfur.

6. (3S,4R, 1′R)-3-(1′-Hydroxyethyl)-4-(N-cinnamyloxycarbonylglycylthio)-2-azetidinone according to claim 5.

* * * * *